United States Patent [19]
Corliss
[11] Plant 4,766
[45] Sep. 15, 1981

[54] EUONYMUS PLANT—CORDOLT VARIETY

[75] Inventor: Clifford D. Corliss, Ipswich, Mass.
[73] Assignee: The Conard-Pyle Company, West Grove, Pa.

[21] Appl. No.: 150,963
[22] Filed: May 19, 1980
[51] Int. Cl.[3] ..... A01H 5/12
[52] U.S. Cl. ..... Plt./63
[58] Field of Search ..... Plt./63
*Primary Examiner*—Robert E. Bagwill
*Attorney, Agent, or Firm*—Burns, Doane, Swecker & Mathis

[57] ABSTRACT

A new and distinct variety of *Euonymus fortunei* which is branch mutation of the Emerald Gaiety variety (i.e., U.S. Plant Pat. No. 1,960) is provided. The new variety possesses smaller leaves than the parent which are attractively variegated in color. More specifically, the mature leaves are deep green and have ivory margins giving the overall plant a silvery appearance when viewed from a distance. Unlike the parent the new variety exhibits a low and broad dense dwarf growth habit which renders it highly suited for use as a mounding ground cover.

2 Drawing Figures

SUMMARY OF THE INVENTION

The new variety was discovered and selected by me during 1973 while present in a cultivated block of plants of the Emerald Gaiety variety (U.S. Plant Pat. No. 1,960) of *Euonymus fortunei* being grown under my direction at the nursery property of Corliss Bros., Inc. at Ipswich, Mass. A branch of one particular plant was discovered having a growth habit, leaf size and leaf appearance which differed from that of the Emerald gaiety variety. This branch was preserved and continued close observation has confirmed its distinctive characteristics which differ from all varieties of *Euonymus fortunei* of which I am aware.

The following combination of characteristics is exhibited by the new variety:

(a) a low and broad dense dwarf growth habit rendering the plant suitable for use as a mounding ground cover, (b) smaller variegated leaves which when mature are deep green with ivory margins giving the overall plant an attractive silvery appearance when viewed from a distance, (c) vigorous growth characteristics, (d) the ability to thrive under a wide range of climatic conditions, and (e) the ability to be sheared within prescribed limits or shaped to a specific form.

Asexual reproduction of my new variety by cuttings has been accomplished at Ipswich, Mass. and West Grove, Pa. Such propagation through at least six generations has demonstrated that the unique combination of characteristics has been established and is transmitted to successive generations.

The new variety has been named the Cordolt variety.

BRIEF DESCRIPTION OF THE PHOTOGRAPHS

The accompanying photographs show a typical specimen of the new variety as depicted in color as true as reasonably possible to make the same in a color illustration of this character. The photographs were made during mid-summer of a representative plant and plant parts thereof two growing seasons following the year of propagation. The subject plant was grown at West Grove, Pa. in an artificial soilless medium.

FIG. 1 illustrates the appearance of a representative plant of the new variety, and FIG. 2 illustrates representative branches of the new variety as well as the appearance of the upper and under surfaces of typical leaves.

DETAILED DESCRIPTION

Figure 2:
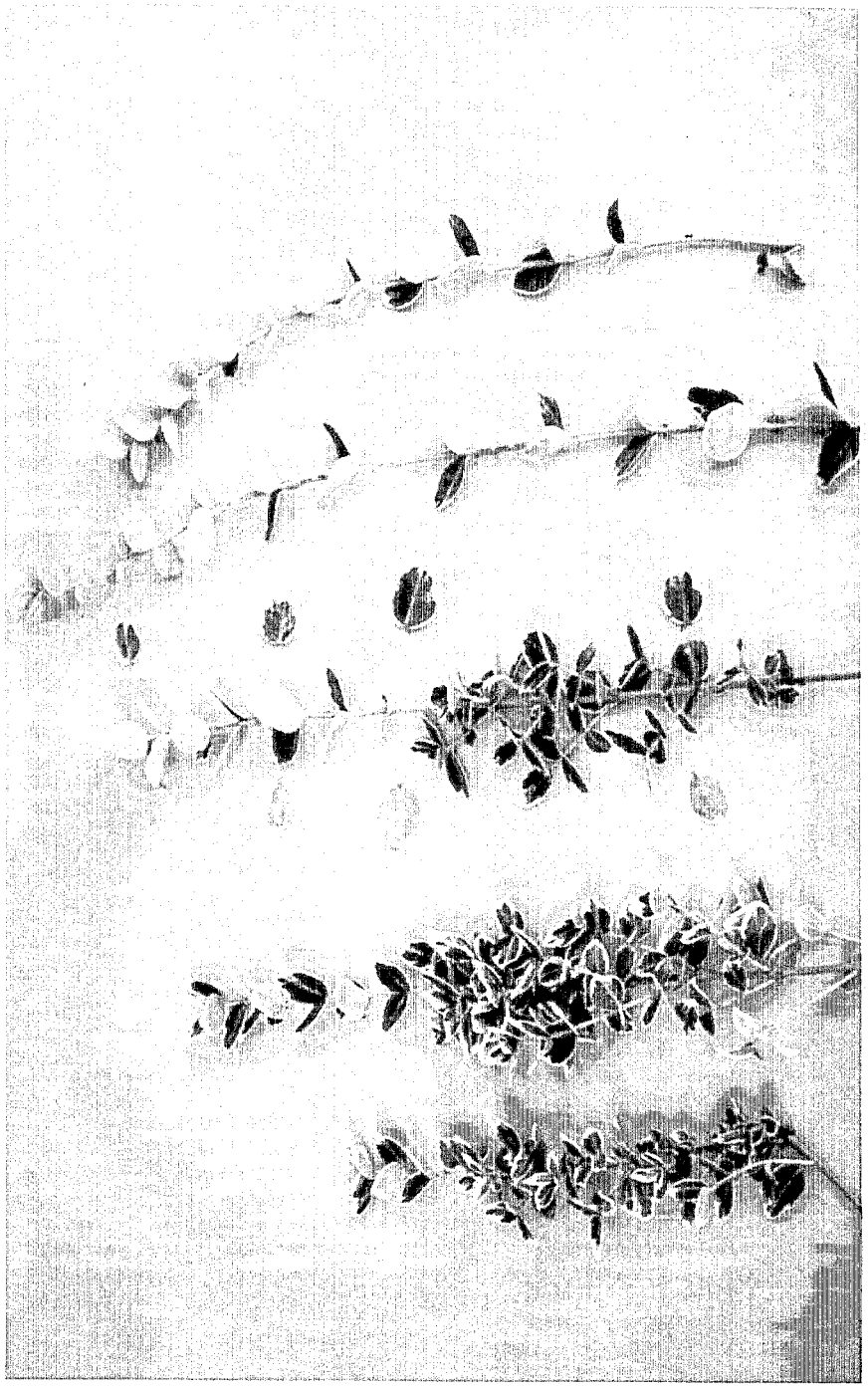

The following is a detailed description of my new variety, with color terminology in accordance with the R.H.S. Colour Chart of the Royal Horticultural Society, London, England. The description was made during mid-summer following the observation of representative plants two growing seasons following the year of propagation which were grown in an artificial soilless medium at West Grove, Pa.

Growth Habit: Dense dwarf. The plants described above commonly possess a height of approximately 18 to 21 inches and a breadth of approximately 15 to 18 inches while the Emerald Gaiety variety commonly possesses a height of approximately 21 to 24 inches and a breadth of approximately 18 to 21 inches under the same growing conditions. The plant is suitable for growing as an attractive mounding ground cover.

Foliage:

*Type.*—Broadleaf evergreen; petioled; opposite.

*Shape.*—From ovate to broad ovate. Base obtuse; apex mostly obtuse, some acute. Margins serrate to serrate-crenate.

*Size.*—Mature leaves on current year's growth are considerably smaller than those of the Emerald Gaiety variety and commonly measure approximately 1.5 to 2.8 cm. in length and approximately 1.4 to 2.3 cm. in breadth. The leaves are expected to increase in size somewhat as the age of the plant increases as is common with other varieties of *Euonymus fortunei.*

*Color-upper surface.*—Mature leaves Green Group 137A edged with irregular slight band of Greyed Yellow Group 162C. The variegated margins do not extend into the leaf nearly as far as those of the Emerald Gaiety variety. When viewed from a distance the overall plant exhibits an attractive somewhat silvery appearance.

*Color-under surface.*—Mature leaves Yellow-Green Group 147C.

Flowers: None observed to date.

Hardiness: Good winter hardiness. The new variety has withstood temperatures of −20° F. when grown at Ipswich, Mass.

Disease and drought resistance: Good.

I claim:

1. A new and distinct variety of *Euonymus fortunei* which is a branch mutation of the Emerald Gaiety variety, substantially as herein shown and described, characterized particularly as to novelty by the unique combination of:

(a) a low and broad dense dwarf growth habit rendering the plant suitable for use as a mounding ground cover, (b) smaller variegated leaves which when mature are deep green with ivory margins giving the overall plant an attractive silvery appearance when viewed from a distance, (c) vigorous growth characteristics, (d) the ability to thrive under a wide range of climatic conditions, and (e) the ability to be sheared within prescribed limits or shaped to a specific form.

* * * * *